(12) United States Patent
Wright et al.

(10) Patent No.: US 11,116,512 B2
(45) Date of Patent: Sep. 14, 2021

(54) DEVICE AND METHOD FOR DISPENSING FOAM

(71) Applicant: PROVENSIS LIMITED, London (GB)

(72) Inventors: David Dakin Iorwerth Wright, London (GB); David Ian Faulkner, London (GB)

(73) Assignee: Provensis Limited, London (GB)

( * ) Notice: Subject to any disclaimer, the term of this patent is extended or adjusted under 35 U.S.C. 154(b) by 0 days.

(21) Appl. No.: 16/066,397

(22) PCT Filed: Feb. 27, 2017

(86) PCT No.: PCT/IB2017/051137
§ 371 (c)(1),
(2) Date: Jun. 27, 2018

(87) PCT Pub. No.: WO2017/145132
PCT Pub. Date: Aug. 31, 2017

(65) Prior Publication Data
US 2019/0000487 A1    Jan. 3, 2019

(30) Foreign Application Priority Data

Feb. 26, 2016 (GB) .................................... 1603397

(51) Int. Cl.
*A61M 5/178* (2006.01)
*A61B 17/12* (2006.01)
(Continued)

(52) U.S. Cl.
CPC ..... *A61B 17/12186* (2013.01); *A61M 5/1782* (2013.01); *A61M 5/3146* (2013.01);
(Continued)

(58) Field of Classification Search
CPC .............. A61M 5/1782; A61M 5/3146; A61M 39/225; A61M 2005/3114; A61M 2005/2123
See application file for complete search history.

(56) References Cited

U.S. PATENT DOCUMENTS

| 6,500,153 B1* | 12/2002 | Sheppard | ........... A61B 17/3401 604/164.01 |
| 2007/0051426 A1* | 3/2007 | Harman | ............... B65D 83/756 141/319 |

(Continued)

FOREIGN PATENT DOCUMENTS

| JP | 2007504872 A | 3/2007 |
| JP | 2007516822 A | 6/2007 |

(Continued)

OTHER PUBLICATIONS

International Search Report for PCT/IB2017/051137, dated Jul. 6, 2017, 3 pages.

*Primary Examiner* — Nathan R Price
*Assistant Examiner* — Courtney B Fredrickson
(74) *Attorney, Agent, or Firm* — Seager, Tufte & Wickhem, LLP

(57) ABSTRACT

A foam transfer or dispensing device is described which dispenses foam from a source of foam, typically a pressurised canister, and which enables efficient purging or air and an initial volume of foam from the device to ensure foam sterility and quality when a syringe is filled from the device. The device comprises a foam inlet arranged for communication with a source of foam, a foam pathway in fluid communication with the foam inlet and comprising a foam outlet, arranged for engagement by a syringe nozzle; and a waste outlet in fluid communication with the foam pathway. The foam pathway comprises a tubular projection arranged to extend through the foam outlet and into a syringe (Continued)

nozzle when a syringe is connected to the foam outlet, which improves the efficiency of the purging process and prevents pooling of air or foam. The device further comprises a means for restricting displacement of material through the waste outlet, so that the user can control the volume of foam that is wasted.

13 Claims, 3 Drawing Sheets

(51) Int. Cl.
    *A61M 5/31* (2006.01)
    *A61M 39/22* (2006.01)
    *B65D 83/14* (2006.01)

(52) U.S. Cl.
    CPC ......... *A61M 39/225* (2013.01); *B65D 83/756* (2013.01); *B65D 83/7532* (2013.01); *A61M 2005/3114* (2013.01); *A61M 2005/3123* (2013.01); *A61M 2039/229* (2013.01)

(56) References Cited

U.S. PATENT DOCUMENTS

| | | |
|---|---|---|
| 2008/0294096 A1 | 11/2008 | Uber, III et al. |
| 2010/0280536 A1* | 11/2010 | Hartwell ............ A61B 17/3203 606/167 |
| 2013/0041258 A1 | 2/2013 | Patrick et al. |
| 2014/0276215 A1 | 9/2014 | Nelson et al. |

FOREIGN PATENT DOCUMENTS

| | | |
|---|---|---|
| WO | 00/72821 | 12/2000 |
| WO | 2005/023678 | 3/2005 |
| WO | 2005/053776 | 6/2005 |

\* cited by examiner

DEVICE AND METHOD FOR DISPENSING FOAM

This application is the U.S. national phase of International Application No. PCT/IB2017/051137 filed 27 Feb. 2017, which designated the U.S. and claims priority to GB Patent Application No. 1603397.9 filed 26 Feb. 2016, the entire contents of each of which are hereby incorporated by reference.

The present invention relates to devices and methods for dispensing foam from a source of foam, e.g. from a pressurised canister which generates foam by passing liquid and gas through a fine mesh. The invention is suitable, in particular, for dispensing a medical foam, for which control of sterility and gas content is essential if the foam is to be injected into a patient e.g. for sclerotherapy of varicose veins.

WO 2005/023678 describes a foam-generating canister and a dispensing device, which transfers foam from the canister to an administration device, for example, a syringe. The dispensing device includes an inlet in communication with a source of foam, a usable foam outlet and a waste bleed outlet, which is in fluid communication with the inlet and which has a higher resistance to flow of foam than that of the usable foam outlet. The differential resistances between the usable foam outlet and the waste bleed outlet, within the device, ensures that foam only flows through the waste bleed outlet when flow is restricted through the useable foam outlet. This allows the user to flush the device of any fluid that is present within the device prior to use by blocking the foam outlet and diverting an initial volume of gas and/or foam through the waste bleed outlet. Once the, initial volume of gas and foam (which is typically air-contaminated and of insufficient quality) has been diverted to waste, the foam outlet is unblocked so that only usable foam of a desired quality is delivered to the foam outlet and, subsequently, administered to a patient. The blocking and unblocking of the useable foam outlet is typically achieved manually, by the user connecting a syringe to the useable foam outlet and holding the syringe plunger in its depressed state to prevent it from filling.

In one specific embodiment, WO 2005/023678 (FIG. 19) provides a foam dispensing device that includes an inlet 718 in communication with a source of foam, a foam outlet 719, a waste outlet 717 and a flexible waste container 706. The foam outlet 719 is a metal cannula that extends into the nozzle of a syringe. Foam is delivered into the syringe nozzle through the metal cannula 719 and displaces air from the nozzle through the waste outlet 717 and into the waste container 706. When the waste container 706 is filled with gas and foam the back-pressure created by delivery of additional foam into the waste chamber causes the foam to flow into the syringe barrel and fills the syringe with foam i.e. the user does not need to manually block the foam outlet and the syringe will fill automatically once the pressure in the waste chamber is sufficiently high to overcome the break-out force of the syringe plunger in the barrel.

The device described above dispenses foam into a syringe and enables both flushing of air and "purging" of foam to be carried out in a semi-automatic manner before foam is collected and administered to a patient. However, the syringe cannot be filled with foam until sufficient material has been purged to fill the waste container 706 such that the pressure reaches a level sufficient to move the syringe plunger. This arrangement means that a new device is required every time a syringe is filled with foam which is inconvenient and leads to undesirable wastage of foam during the dispensing process. For example, after an initial injection of foam to a varicosity, the administering physician may choose to make a second, smaller injection, for example to treat tributary veins. In this case, more foam may be purged than is actually administered to the patient, which is undesirable from a practical and regulatory perspective.

The present invention provides a device which can be used to dispense foam in the same way as described above but which is not limited to single use. The device of the present invention has a similar design to that described in WO 2005/023678 but comprises a useable foam outlet with improved geometry for more efficient purging and filling of a syringe, which is attached to it. The device further comprises a modified waste outlet, which includes a means for preventing the flow of gas and/or foam into a waste chamber thus eliminating the need to completely fill the waste container prior to dispensing the foam. Delivery of foam into the syringe nozzle displaces the contents of the syringe nozzle into a waste outlet as in the prior art device but the geometry of the useable foam outlet prevents pooling of air or foam in the syringe which can occur in the restricted volume of a typical syringe nozzle. The modified waste outlet enables control of the volume of foam that enters the waste chamber such that, after a first syringe is filled, additional syringes can be filled using the same device (until the waste chamber is full) thereby simplifying the foam preparation process for the user. In practice, this enables a physician to use the same device when treating a single patient with multiple injections without having to replace the device with each injection but still allowing replacements between patients.

In a first aspect the present invention provides a device for dispensing foam from a source of foam, the device comprising:
  a foam inlet arranged for communication with a source of foam;
  a foam pathway in fluid communication with the foam inlet and comprising a foam outlet arranged for connection to a syringe nozzle; and
  a waste outlet in fluid communication with the foam pathway,
wherein the foam pathway comprises a tubular projection arranged to extend through the foam outlet and into a syringe nozzle when it is connected to the outlet, and wherein the device further comprises a means for restricting displacement of material into the waste outlet.

The means for restricting displacement of material, e.g. liquid, gas or foam, into the waste outlet allows a user to control the amount of air and foam that is displaced from a syringe as waste before the syringe is filled. By preventing displacement of material through the waste outlet the user can allow the syringe to be filled with foam either by pressure provided from the source of foam or by simple aspiration of the syringe, i.e. withdrawal of the syringe plunger. This arrangement provides a solution to the technical problem of allowing more than one syringe to be filled with foam using a single device while also potentially reducing the amount of foam that is wasted when purging syringes. These advantages serve to improve usability of foam products in treating vascular disease.

The means for restricting displacement of material into the waste outlet can be a valve or an arrangement of pathways that provides increased resistance to foam within the waste outlet relative to the resistance of the syringe to be filled. Preferably flow of foam into the waste outlet (and a waste chamber) is controlled with a valve. The valve may operate automatically to close the waste outlet on displacement of a pre-set volume of foam or after a pre-set time has elapsed after the process has begun. The valve may be manually controlled by the user but, preferably, is a pressure-valve that opens in response to increased pressure in the foam pathway and closes when that pressure decreases. Such pressure changes can easily be achieved by the user holding a syringe plunger in place until sufficient pressure is built up in the foam pathway to open the valve. Once the valve is open and foam has started to flow through the waste outlet, the syringe plunger may be released, allowing it to move back under the pressure of the foam pathway and causing the syringe to fill with foam. The filling of the syringe with foam will reduce the pressure in the foam pathway sufficient to close the valve and prevent further flow through the waste outlet. Preferably the valve is operated manually as this provides a simple and cost-effective solution to the problem of allowing more than one syringe to be filled with foam using a single device while also potentially reducing the amount of foam that is wasted when purging syringes.

The device comprises a foam inlet through which foam is provided from a source of foam. The source of foam may be provided together with the device or it may be provided separately from it. It will be understood that where a source of foam is provided separately, the foam inlet will comprise a connector to allow secure attachment and fluid communication with the source of foam. Such connectors are well known in the art. Typically, the source of foam is a pressurized canister as described in WO 2005/023678 and in WO 00/72821.

The foam pathway is in fluid communication with the foam inlet such that a flow path is defined therebetween. The foam pathway is defined by the distal end of the flow path and includes a foam outlet, in the form of an aperture. The aperture is typically in the form of a luer or other connection which provides a seal between the foam pathway and the nozzle of a standard syringe. The foam pathway comprises a tubular protrusion that is designed to extend through and beyond the foam outlet, such that when a syringe is connected to the foam outlet the tubular protrusion extends into the syringe nozzle, without contacting any part of the inside of the nozzle and without interfering with the seal created between the syringe and the foam pathway. The tubular protrusion has the effect of providing a vent within the syringe nozzle, such that foam delivered to the syringe nozzle efficiently displaces the contents of the nozzle into the waste outlet. As foam flows directly into the syringe nozzle, and the "dead space" between the nozzle and the syringe plunger, it fills the nozzle and displaces its contents (i.e. air and an initial volume of foam) from the nozzle into the waste outlet. The tubular protrusion is conveniently proportioned to allow displacement of syringe nozzle contents from adjacent the syringe plunger into the waste outlet such that the syringe nozzle is filled with foam. This has been found to be effective in displacing the air from the syringe nozzle and into the waste outlet as more foam is delivered and prevents pooling within the inner volume of the nozzle The tubular projection can be made of any material that is suitable for medical device applications i.e. materials which are sterile or can be sterilized. Typically, the protrusion will be formed from a rigid or non-deformable material that will resist breakage or deformation, if accidentally knocked prior to or during connection of a syringe to the foam outlet. Suitable materials will be inert to the foam constituents and include metals, such as aluminium and stainless steel, and plastics such as styrenic block copolymers (TPE-s), polyolefin blends (TPE-o), elastomeric alloys (TPE-v or TPV), thermoplastic polyurethanes (TPU), thermoplastic copolyesters and thermoplastic polyamides. Preferably the tubular projection is a metal tube, formed from stainless steel.

A standard syringe nozzle comprises a frustoconical chamber, for example a luer slip, that tapers to an aperture having an internal diameter of between 1.5 mm and 2.5 mm. Typically the syringe nozzle aperture has an internal diameter of approximately 2 mm, and therefore it is desirable that the tubular projection has an external diameter of less than 2 mm to allow it to extend into the syringe nozzle. In use, when the tubular projection is extended into a syringe nozzle, it is necessary that sufficient clearance is provided between its circumferential edge and the internal edge of the syringe nozzle aperture to allow delivery of foam into the syringe nozzle or displacement of the contents of the syringe nozzle into the waste outlet. Therefore, the protrusion will typically have an external diameter between 0.5 mm and 1.5 mm. Preferably the external diameter of the protrusion is between 0.75 mm and 1.25 mm, and more preferably the external diameter is approximately 1 mm.

The device may be used with a standard syringe having a plunger depressed (i.e. in the form in which syringes are normally provided) to reduce the volume of air that needs to be purged. However, for certain uses, particularly when small volume syringes are being used, as is typical for cosmetic indications, it is desirable to use a 'pre-cracked' syringe. These are syringes which are provided with the plunger pulled back in the syringe barrel so as to reduce the pressure that is needed to force back the plunger as the syringe is filled with foam. Syringes in this format are purged in effectively the same way as the standard syringes described above, except that the volume of air to be purged is defined by the volume of the syringe nozzle and the barrel volume created by pulling back the plunger. For these applications, the tubular protrusion can be elongated such that is extends through the nozzle and into the barrel to a point that is in close proximity to the syringe plunger. This is advantageous as it allows displacement of air from the barrel of the syringe and the nozzle into the waste outlet. Provided the flow of foam is not blocked, the tubular projection may contact the syringe plunger to ensure that all of the air is displaced by foam and reduce the risk that any air is trapped as foam fills the volume.

Where foam is provided from a pressurized canister device, it will be understood that foam initially generated by the device may not be of the required specification until all of the foam pathway has been flushed of fluid. The present invention enables purging of out of specification foam by simply continuing to dispense foam after air has been purged while allowing flow into the waste outlet to continue, as described above, until an initial volume of foam has been displaced from the syringe nozzle (or barrel) and diverted through the waste outlet into a waste chamber. Optionally, a waste chamber is contained in a common housing with the foam inlet and foam outlet, and is connected to the waste outlet, such that waste is collected for disposal. In this regard the waste chamber can be removable so that any waste foam collected can be discarded after each administration. Alternatively, and preferably the waste chamber is contained within the device and the entire device is disposed of after each course of administration of foam (for example, between patients), to reduce the risk of contamination. The incorporation of a waste chamber into the device provides an enhanced experience for the user, as waste foam is never collected into the syringe. Depending on whether or not the device is intended for single or multiple use, the volume of the waste chamber can be defined to ensure it is of sufficient size to capture all of the waste foam. Preferably the waste chamber is of a predetermined fixed volume that captures all purged air and poor quality foam. Preferably the waste chamber is formed of a transparent material, and is visible through a transparent section of the device/housing, such that the user can see when foam has started to fill the waste chamber and, consequently, can be confident that initial "poor quality" foam has been diverted to waste. If desired, the waste chamber can be vented to allow purged air to escape the chamber before it is filled with foam.

It is not essential that the device is used with a pressurised source of foam. Provided there is sufficient driving force to fill a syringe nozzle and displace air, the syringe may be aspirated as normal, by pulling back the syringe plunger until the desired quantity of foam has been collected. This arrangement is advantageous as it is simple and inexpensive to manufacture and it doesn't require a power source or any additional equipment to operate.

The device can optionally comprise a source of foam in communication with the foam inlet. Such a device simplifies use or the user by combining the production and dispensing of foam for administration to a patient. The source of foam can be pressurized canister system comprising a single can or two cans. Preferably the source of foam comprises a canister charged with liquid and gas under pressure. Such a source of foam is advantageous as it provides foam in a simple format that is easy to use and that has been approved for use in the USA for producing therapeutic foam.

In a second aspect the present invention provides a kit according to the first aspect of the invention and a syringe.

The second aspect of the invention provides the same optional features and advantages as described above for the first aspect. Providing the device and syringe together in a kit is advantageous as it ensures that syringes are used which are of the appropriate size for connecting to the foam outlet and are suitable for administration of foam to patients, for example, pre-cracked syringes may be required for particular indications, as discussed above. In a particular embodiment the kit is provided with a syringe pre-connected to the foam outlet. This is particularly advantageous in reducing handling by the user and ensuring sterility.

In a third aspect the present invention provides a method of dispensing foam using a device according to the first aspect of the invention comprising the steps of:
connecting a syringe to the foam outlet;
causing foam to flow from a source of foam into the foam inlet and simultaneously holding a plunger of the syringe in a fully depressed position until a volume of foam has displaced the contents of the syringe dead space and an initial volume of foam into the waste outlet; and
releasing the plunger to fill the syringe with foam.

The third aspect of the invention provides the same optional features and advantages as described above for the first and second aspects. The method allows the user to dispense foam into a syringe while simultaneously purging the contents of the syringe nozzle and removing the need for an additional syringe purging step to ensure safe administration of foam to the patient. The method above is equally applicable to the situation when the device is provided in the form of a kit, with syringe pre-connected to the foam outlet, as described above. In this embodiment, it will be understood that the first step of connecting the syringe is not necessary.

Further features and advantages of the invention will be apparent from the following description of a specific embodiment, which is made with reference to the accompanying drawing.

Figure 1:
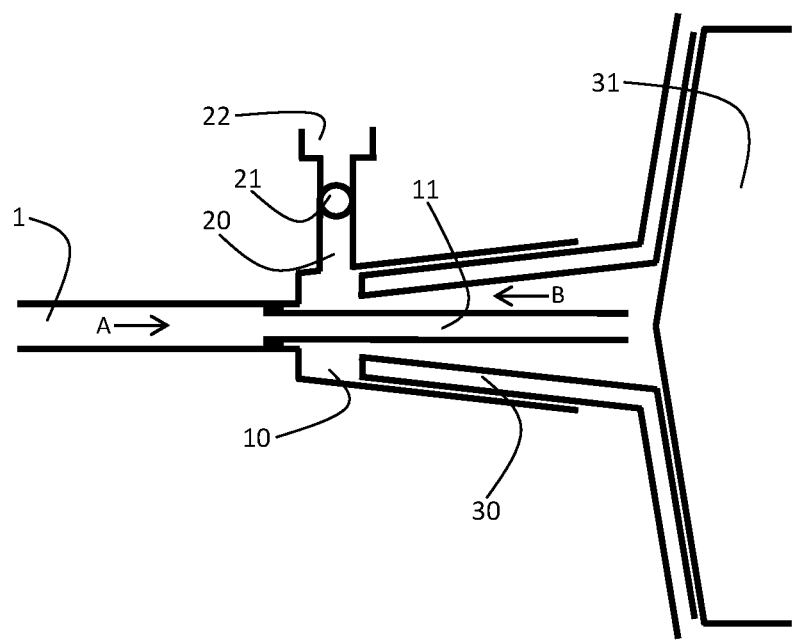
FIG. 1 shows a schematic view of a portion of a first embodiment according to the first aspect of the invention together with a syringe nozzle.

A portion of a first embodiment according to the first aspect of the invention is shown in FIG. 1, in which a foam pathway (10) is engaged by a syringe nozzle (30) as these elements would be arranged while the device is in use dispensing foam into a syringe.

The foam pathway (10) is in fluid communication with a foam inlet (1), through which foam is supplied from a pressurized canister system as described in WO 00/72821 which provides a source of foam, under pressure (not shown). Foam arrives at the foam inlet (1) and flows in the direction of the arrow A, entering the syringe nozzle (30) via a metal tube (11) which extends out from the foam outlet and into the inner volume of the connected syringe nozzle.

The foam is delivered into the syringe nozzle (30) at the surface of the syringe plunger (31) such that air in the syringe nozzle (30) is displaced in the direction of the arrow B out of the syringe nozzle (6) through the foam pathway (10) and into the waste outlet (20).

As further foam is delivered to the syringe nozzle (30) air in the waste outlet (20) is displaced through a valve (21) into a waste chamber (22).

Once the syringe nozzle (30) is filled with foam, a portion of foam is displaced into the waste outlet (20), through the valve (21) and into the waste chamber (22).

The valve (21) is then closed manually by the user so that no further foam or air can pass through the waste outlet (20) into the waste chamber (22), and this leads to an increase in pressure within the foam pathway (10) and the syringe nozzle (30). The increased pressure forces the syringe plunger (31) to move toward a more withdrawn position, and consequently the syringe fills with foam as it is delivered through the metal tube (11).

The syringe is filled with foam and contains no air. The user is not required to carry out a purge step to remove trapped air and can have increased confidence that the foam in the syringe is less likely to cause air embolism in the patient.

Figure 2:
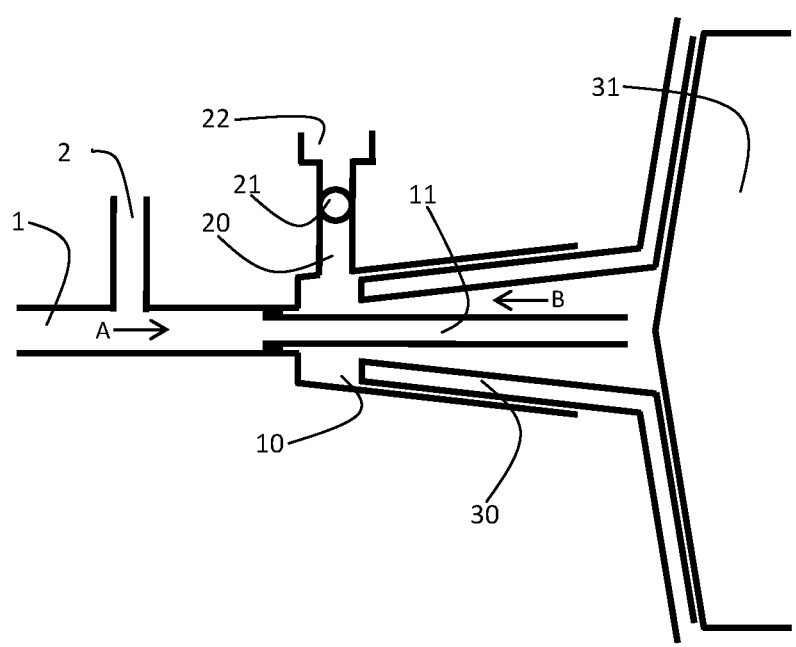
FIG. 2 shows a schematic view of a portion of a second embodiment according to the first aspect of the invention together with a syringe nozzle.

A second embodiment according to the first aspect of the invention is shown in FIG. 2.

The device of this embodiment is similar to that of the first embodiment and is shown engaged by a syringe nozzle (30) as these elements would be arranged while the device is in use. However, it includes a branch pathway (2) in the foam inlet (1). Foam arrives at the foam inlet (1) from the source of foam (not shown), and it is prevented from flowing into the foam pathway (10) because the valve (21) in the waste outlet (20) is closed. Instead the foam flows into the branch pathway (2) where it is observed by the user. When the foam reaches the required quality the user opens the valve (21), and the device functions in the same manner as the first embodiment to fill the syringe with foam.

Figure 3:
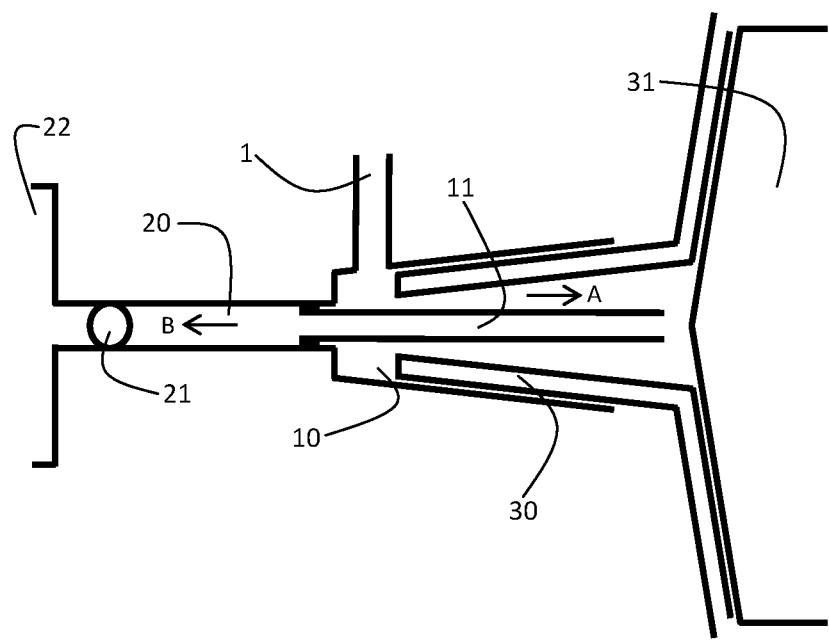
FIG. 3 shows a schematic view of a portion of a third embodiment according to the first aspect of the invention together with a syringe nozzle.

A third embodiment according to the first aspect of the invention is shown in FIG. 3 engaged with a syringe nozzle (30) as these elements would be arranged while the device is in use.

The foam pathway (10) is in fluid communication with a foam inlet (1), through which foam is supplied from a pressurized canister system as described in WO 00/72821 which provides a source of foam, under pressure (not shown). Foam arrives at the foam inlet (1) and flows into the foam pathway (10) from where it enters the syringe nozzle (30) and travels in the direction of the arrow A. As the foam travels toward the surface of the syringe plunger (31) it displaces air from the syringe nozzle into the metal tube (11) and further into the waste outlet (20).

As more foam is delivered to the syringe nozzle (30) air in the waste outlet (20) is displaced through a valve (21) into a waste chamber (22).

Once the syringe nozzle (30) is filled with foam, a portion of foam is displaced through the metal tube (11), into the waste outlet (20), through the valve (21) and into the waste chamber (22).

The valve (21) is then closed manually by the user so that no further foam or air can pass through the waste outlet (20) into the waste chamber (22), and this leads to an increase in pressure within the foam pathway (10) and the syringe nozzle (30). The increased pressure forces the syringe plunger (31) to move toward a more withdrawn position, and consequently the syringe fills with foam as it is delivered through the foam pathway (10).

The invention claimed is:

1. A device for dispensing foam from a source of foam, the device comprising:
   (a) a foam inlet arranged for communication with a source of foam;
   (b) a foam pathway in fluid communication with the foam inlet and comprising a foam outlet, arranged for engagement by a syringe nozzle; and
   (c) a waste outlet in fluid communication with the foam pathway,
   wherein the foam pathway comprises a tubular projection arranged to extend through the foam outlet and into a syringe nozzle when a syringe is connected to the foam outlet, and wherein the device further comprises a pressure valve that opens and closes in response to pressure changes, the pressure valve controllably restricting displacement of material from the foam pathway through the waste outlet, wherein the pressure valve opens in response to an increased pressure in the foam pathway, and closes in response to a decrease in that pressure.

2. A device according to claim 1 wherein a waste chamber is provided in fluid communication with the waste outlet.

3. A device according to claim 2 wherein at least a portion of the foam inlet, a portion of the foam pathway, a portion of the waste outlet or a portion of the waste chamber is transparent to allow inspection of foam in the device.

4. A device according to claim 1 wherein the tubular projection comprises a metal tube.

5. A device according to claim 4 wherein the metal tube has an external diameter between 0.5 mm and 1.5 mm.

6. A device according to claim 5 wherein the metal tube has an external diameter of 1 mm.

7. A device according to claim 1 wherein the tubular projection extends across the entire length of the syringe nozzle.

8. A device according to claim 1 wherein the tubular projection is arranged to make physical contact with the syringe plunger.

9. A device according to claim 1 comprising a source of foam in communication with the foam inlet.

10. A device according to claim 9 wherein the source of foam comprises a canister charged with liquid and gas under pressure.

11. A kit comprising a device as claimed in claim 1 and a syringe.

12. A kit according to claim 11 wherein the syringe is connected to the foam pathway of the device via the foam outlet which is arranged for engagement by the syringe nozzle.

13. A method of dispensing foam using a device according to claim 1 comprising the steps of:
   (a) connecting a syringe to the foam pathway;
   (b) causing foam to flow from the source of foam into the foam inlet and simultaneously holding a plunger of the syringe in a fully depressed position until a volume of foam has displaced the contents of the syringe nozzle and flowed into the waste outlet; and
   (c) releasing the plunger to fill the syringe with foam.

* * * * *